United States Patent
Schnell

[11] 4,234,428
[45] Nov. 18, 1980

[54] DUAL MEMBRANE MASS TRANSFER DEVICE

[75] Inventor: William J. Schnell, Wheeling, Ill.

[73] Assignee: Baxter Travenol Laboratories, Inc., Deerfield, Ill.

[21] Appl. No.: 950,535

[22] Filed: Oct. 12, 1978

[51] Int. Cl.$^3$ .............................................. B01D 31/00
[52] U.S. Cl. ................................. 210/321 B; 210/314; 210/346; 210/433 M; 210/486
[58] Field of Search ...................... 210/22, 23 H, 23 R, 210/314, 321 B, 346, 486, 433 M

[56] References Cited

U.S. PATENT DOCUMENTS

| | | | |
|---|---|---|---|
| 3,362,540 | 1/1968 | Bluemle | 210/321 |
| 3,579,441 | 5/1971 | Brown | 210/346 |
| 3,591,493 | 6/1968 | Zeineh | 210/22 |
| 3,707,234 | 12/1972 | Salemi | 210/433 M |
| 3,734,851 | 5/1973 | Matsumura | 210/22 |
| 3,783,127 | 1/1974 | Cook et al. | 210/321 A |
| 3,962,075 | 6/1976 | Fialkoff et al. | 210/22 A |
| 4,016,081 | 4/1977 | Martinez et al. | 210/321 B |
| 4,024,059 | 5/1977 | Sausse | 210/195 R |

FOREIGN PATENT DOCUMENTS

| | | | |
|---|---|---|---|
| 2443185 | 3/1976 | Fed. Rep. of Germany | 211/23 F |
| 2397197 | 3/1979 | France | 210/321 B |

*Primary Examiner*—Charles N. Hart
*Assistant Examiner*—E. Rollins Cross
*Attorney, Agent, or Firm*—Paul C. Flattery; George H. Gerstman

[57] ABSTRACT

A hemodialysis apparatus is provided in which two blood compartments are formed by two different types of membranes. One membrane is a relatively high flux membrane, with relatively high hydraulic permeability, and the other membrane is a relatively low flux hemodialysis membrane. The blood compartment associated with the high flux membrane will be separated from the blood compartment associated with the low flux membrane. In use, dialyzing solution flows through only a dialysate compartment adjacent to the low flux membrane to accomplish diffusion at low transmembrane pressures. No dialyzing fluid perfuses the compartment adjacent the high flux membrane, but high transmembrane pressures draw ultra-diffusate into this compartment for collection and measurement of fluid loss in the patient.

9 Claims, 4 Drawing Figures

DUAL MEMBRANE MASS TRANSFER DEVICE

BACKGROUND OF THE INVENTION

The present invention concerns a novel hemodialysis apparatus and, more particularly, a membrane hemodialysis apparatus in which two different types of membranes are used so as to provide, simultaneously, significant ultrafiltration in a first compartment and significant dialysis with relatively insignificant ultrafiltration in another compartment.

During normal dialysis, patients susceptible to hypotensive episodes may suffer nausea and/or disequilibrium. Such patients commonly utilize sequential dialysis to alleviate these problems. In sequential dialysis, water is first removed from the patient by ultrafiltration, with no dialysate flow. After ultrafiltration is achieved without utilizing dialyzing solution, the patient subsequently undergoes dialysis with dialyzing solution and a minimum transmembrane pressure gradient, so as to have minimum ultrafiltration.

It is an object of the present invention to achieve the results of sequential dialysis by utilizing apparatus which subjects the patient to both ultrafiltration and dialyzing processes concurrently instead of sequentially.

Another object of the present invention is to provide a unitary encased hemodialysis device having multiple blood compartments formed by two different types of membranes, with some of the compartments being adapted for ultrafiltration processing and the other compartments being adapted for dialysate solution diffusion.

A further object of the present invention is to provide a unitary hemodialysis apparatus that is capable of performing both phases of dialysis simultaneously.

Still another object of the present invention is to provide a hemodialysis apparatus utilizing a high flux type of membrane and a low flux type of membrane, with the different membranes being exposed to different compartments and with the compartments associated with the low flux membrane being segregated from the compartments associated with the high flux membrane. Normal dialysis can then occur through the low flux membrane while ultradiffusion can occur simultaneously with the high flux membrane. Since both processes of diffusion and ultradiffusion are occuring simultaneously, dialysis time can be minimized.

Other objects and advantages of the present invention will become apparent as the description proceeds.

SUMMARY OF THE INVENTION

In accordance with the present invention, an apparatus is provided for the treatment of blood by hemodialysis having a stack of membrane support plates which support membranes on opposite sides thereof and form open volumes between the membrane support plates and the membranes supported thereon. The improvement comprises a plurality of membrane support plates which are spaced from each other to form blood paths in the spacing between the membrane support plates. A relatively high flux membrane, with relatively high hydraulic permeability, is supported on one side of each of the membrane support plates and forms an open volume between the relatively high flux membrane and its respective membrane support plate. A relatively low flux membrane is supported on the opposite side of each of the membrane support plates and forms an open volume between the low flux membrane and its respective membrane support plate.

The open volumes between the relatively high flux membranes and the respective membrane support plates comprise a low pressure path to provide significant ultrafiltration, and the open volumes between the relatively low flux membranes and the respective membrane support plates comprise a dialysate solution path to provide significant dialysis and relatively insignificant ultrafiltration.

In the illustrative embodiment, the one sides of the membrane support plates are oriented in a common direction. In this manner, each of the relatively low flux membranes will face a relatively high flux membrane on opposite sides of the blood path formed in the spacings between the membrane support plates.

In the illustrative embodiment, a blood manifolding path extends through the stack. Closing means are provided for sealing the membranes on opposite sides of each membrane support plate to each other adjacent the blood manifolding path. The closing means are spaced from each other to define a blood path therebetween and are independent of each other. In this manner, the closing forces generated by one of the closing means on its respective membranes are independent of the closing forces generated by other closing means on their respective membranes.

A more detailed explanation of the invention is provided in the following description and claims, and is illustrated in the accompanying drawings.

DETAILED DESCRIPTION OF THE ILLUSTRATIVE EMBODIMENT

In a copending application filed in the names of Jimmy L. Miller and William J. Schnell, U.S. application Ser. No. 883,457, filed Mar. 6, 1978 now U.S. Pat. No. 4,154,792, a novel distribution system for fluid treatment apparatus is disclosed. I have discovered that an apparatus employing structure similar to that disclosed in Miller and Schnell application Ser. No. 883,457, but with certain modifications, may be utilized to perform both phases of dialysis simultaneously.

Figure 1:
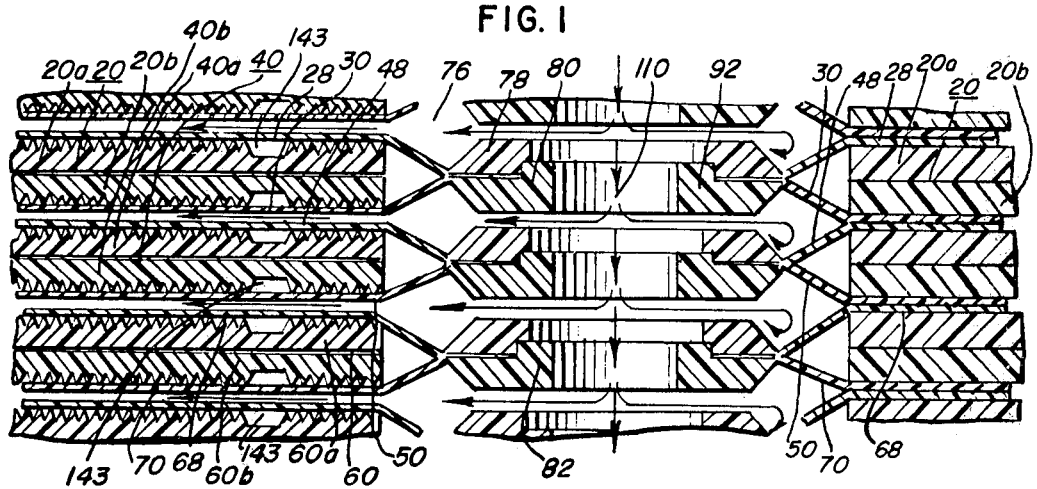
FIG. 1 is a fragmentary cross-sectional view of a membrane stack constructed in accordance with the principles of the present invention.
Figure 3:
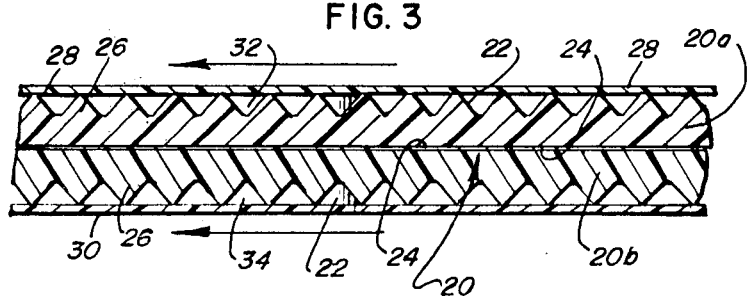
FIG. 3 is a fragmentary, cross-sectional view of a membrane support plate with a pair of membranes being supported thereby.

Referring first to FIG. 1, a first membrane support plate 20 is formed of two identical halves 20a and 20b. Referring to FIG. 3, it is seen that membrane support plate half 20a has a membrane support surface 22, and the underside thereof is a planar surface 24. Membrane support plate half 20b, which is identical to membrane support plate half 20a, has its corresponding planar underside abutting the planar underside 24 of membrane support plate half 20a to form first membrane support plate 20.

Since all of the membrane support plates are identical in construction, only membrane support plate 20 need be discussed in detail. It can be seen that membrane support plate 20 has oppositely positioned membrane support surfaces 22 which carry a plurality of cones 26 upon which membranes 28 and 30 are supported. Further, an open volume 32 is provided between the membrane support plate 20 and membrane 28 and an open volume 34 is provided between the membrane support plate 20 and membrane 30, as shown most clearly in FIG. 3. It is to be understood that while a conical membrane support plate surface is illustrated herein, many other configurations may be used in obtaining proper fluid distribution.

Membrane 28 is a relatively high flux membrane while membrane 30 is a relatively low flux membrane. As used herein, the term "relatively high flux membrane" connotes a membrane with relatively high hydraulic permeability as contrasted to a "relatively low flux membrane". Examples of a relatively high flux membrane are polyacrylonitrile and polycarbonate. A "relatively low flux membrane" is the more conventional hemodialysis membrane, such as Cuprophan ®, which is commonly used in dialysis as the membrane which separates the blood path from the dialysate solution path. These membranes are thin and flexible, but have been shown as relatively thick in the drawings for clarity.

Thus while membrane 28 is a relatively high flux membrane, membrane 30 is a relatively low flux membrane. As will be discussed in more detail below, the open volume 32 forms a low pressure path so that the high transmembrane pressure will draw ultra-diffusate into this open volume 32 for collection and measurement of fluid loss in the patient. Open volume 34 forms a dialysate solution path to provide significant dialysis, but relatively insignificant ultrafiltration.

Thus as a result of the low flux membrane 30 and the relatively low transmembrane pressure, there will be essentially no ultrafiltration through membrane 30.

Referring to FIG. 1, a second membrane support plate 40 is shown, comprising top half 40a and bottom half 40b, identically in the manner that membrane support plate 20 comprises top half 20a and bottom half 20b. Second membrane support plate 40 supports third membrane 48, which is a relatively high flux membrane, and fourth membrane 50, which is a relatively low flux membrane. Second membrane support plate and membranes 48 and 50 supported thereby are identical to first membrane support plate 20 and membranes 28 and 30 supported thereby.

Likewise, a third membrane support plate 60 comprising top half 60a and bottom half 60b is provided for supporting membranes 68 and 70. Membrane 68 is a relatively high flux membrane while membrane 70 is a relatively low flux membrane. Likewise, third membrane support plate 60 and membranes 68 and 70 supported thereby are identical to membrane support plates 20 and 40 and membranes 28, 30 and 48, 50, respectively, supported thereby.

It is to be understood that while first, second and third membrane support plates 20, 40 and 60, respectively, are shown, the dialyzer may contain a much larger number of membrane support plates which support membranes and are constructed identically to membrane support plate 20.

Figure 4:
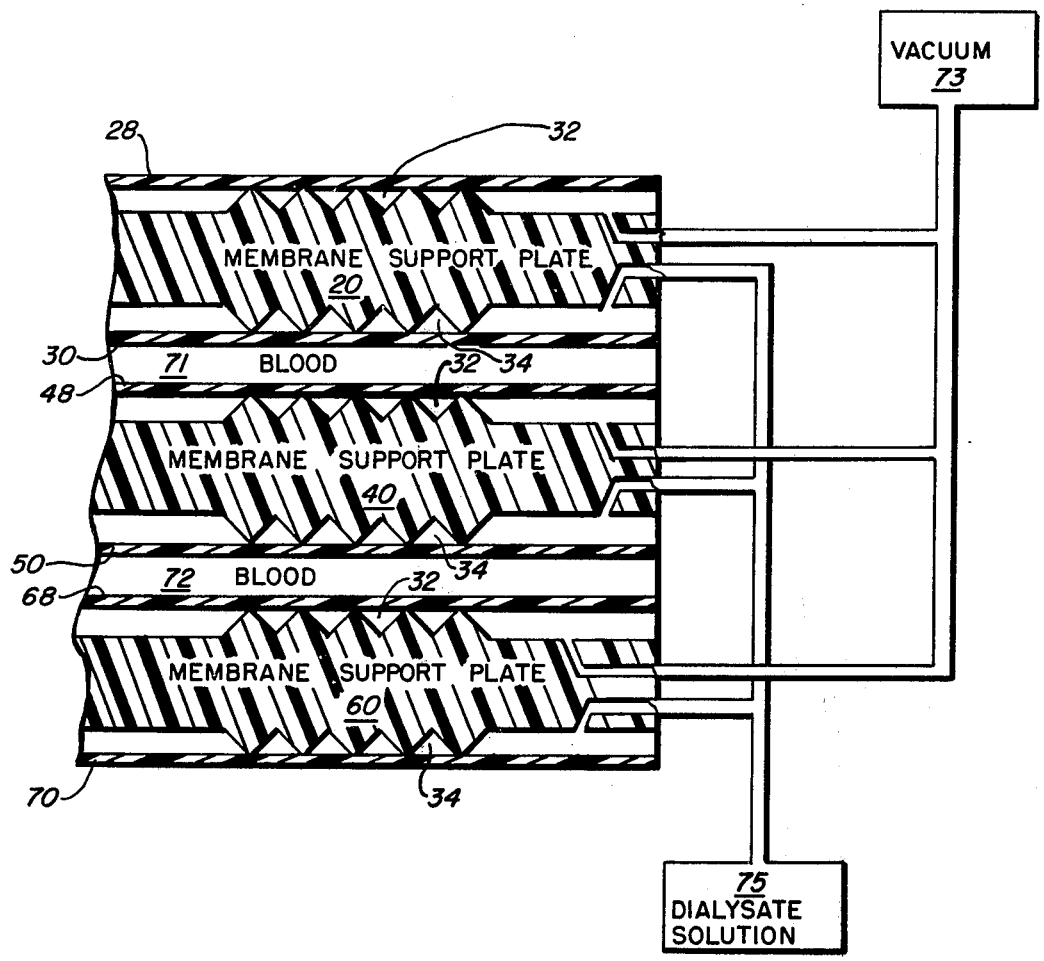
FIG. 4 is a diagrammatic view of blood treatment apparatus constructed in accordance with the principles of the present invention.

Referring now to FIG. 4, a diagrammatic view of the dual membrane distribution system is illustrated therein. It can be seen that membrane support plates 20, 40 and 60 are spaced from each other to form blood paths 71 and 72. High flux membranes 28, 48 and 68 are supported on one side of each of membrane support plates 20, 40 and 60, respectively. Low flux membranes 30, 50 and 70 are supported on the opposite sides of each of the membrane support plates 20, 40 and 60, respectively. Each of the low flux membranes 28, 48 and 68 are oriented in the same direction so that the low flux membranes will be facing the high flux membranes on opposite sides of the blood compartments 71, 72.

The open volumes 32 form ultrafiltrate compartments. To this end, a low pressure path is formed within open volumes 32 by coupling open volumes 32 to a vacuum pump 73, to thereby create a high transmembrane pressure and draw water from the blood. Open volumes 32 may be interconnected to form an ultrafiltrate compartment, which will be segregated from the dialysate solution compartment formed by open volumes 34.

Thus open volumes 34 may be interconnected and coupled to a source of dialysate solution 75 so as to form a dialysate solution path between the membrane support plates and the low flux membranes 30, 50, 70. Normal dialysis can occur through the low flux membranes while ultrafiltration occurs simultaneously through the high flux membranes. The dialyzing solution flows only through open volumes 34 and no dialyzing solution perfuses the open volumes 32.

It is preferred that a non-distensive high flux membrane be utilized and that the low flux membrane have anisotropic properties to effectively aid in the blood side distribution, because distinct fluid channels will be formed by the "sag" of the anisotropic membrane. It has been found that this will simplify the design of the product.

Referring again to FIG. 1, the membrane support plates define openings 76 which are aligned and into which are positioned grommets for closing the membranes supported by each membrane support plate. A grommet 78 is associated with membrane support plate 20for closing first and second membranes 28, 30, respectively. Likewise, a grommet 80 is positioned in opening 76 adjacent second membrane support plate 40 for closing third and fourth membranes 48 and 50. A third grommet 82 is positioned in opening 76 adjacent third membrane support plate 60 for closing membranes 68 and 70. Additional grommets are positioned in the openings 76 of each other membrane support plate for closing the membranes supported by each membrane support plate.

Figure 2:
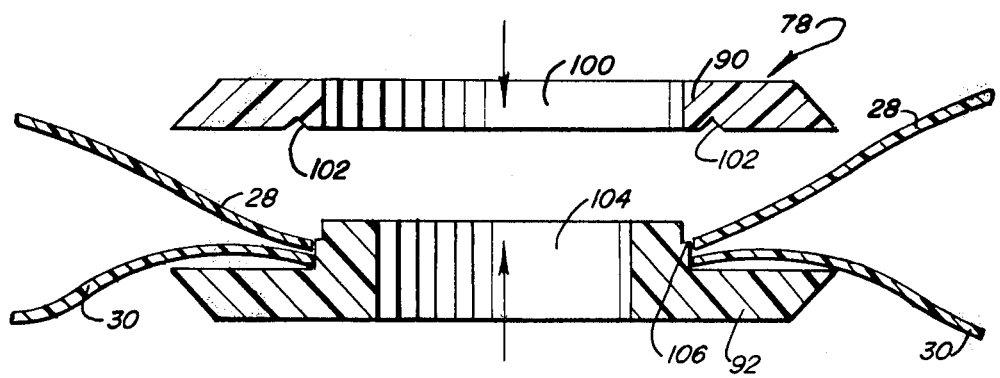
FIG. 2 is an enlarged cross-sectional view of a grommet of the type which can be used in the stack of FIG. 1.

Since each of the grommets is identical, the construction of grommet 78 will be explained in detail, referring to FIG. 2. Grommet 78 comprises an upper ring 90 and a lower ring 92 which are ultrasonically welded to each other to close membranes 28 and 30. Each of the membranes is pre-punched so that when it overlies the membrane support plate openings in the membrane will align with blood openings defined by the membrane support plate.

Upper ring 90 defines a central opening 100 and is provided with a weld trap 102 annularly about the underside of ring 90. Lower ring 92 defines a central opening 104 and includes a shear joint 106 which operates during sonic welding in accordance with principles wellknown in the ultra sonic welding art. Top ring portion 90 and bottom ring portion 92 are sonically welded together to fuse and form a closing means for closing the membranes supported by the membrane support plates. The central opening defined by the grommets form a blood manifolding path 110 which permits the blood to flow freely through this path and through the blood paths 71, 72 (FIG. 4) between adjacent membranes as indicated by the arrows illustrated in FIG. 1.

It can be seen that each of the grommets 78, 80, 82, etc. close the membranes supported by an adjacent membrane support plate and each grommet is spaced from the other to define a blood flow path therebetween. Further, each grommet is independent of the other whereby the closing forces on each pair of membranes supported by a membrane support plate are independent of the closing forces on the other pair of membranes supported by other membrane support plates.

Although a grommet closure system is shown, it is to be understood that other closure systems may be used. For example, the membranes 28, 30 may be heat sealed or may be cement bonded instead of being closed by means of a grommet. It is preferred that each of the membrane pairs be closed in the same manner as the closure for the other membrane pairs.

Although there are many types of devices that could be used to stack the parallel membrane support plates 20, 40, 60, etc. and support the membranes 28, 30, 48, 50, 68, 70, etc., an example of a suitable device is disclosed in copending U.S. application Ser. No. 732,233, filed Oct. 14, 1976, in the name of William J. Schnell for "Dialyzer Casing".

It is seen that a unitary hemodialysis apparatus of the parallel plate configuration has been disclosed, with the ultrafiltrate compartment formed by a high flux membrane and a dialysate compartment formed by a low flux membrane. Normal dialysis occurs through the low flux membrane while ultradiffusion occurs simultaneously through the high flux membrane, thereby performing both phases of dialysis simultaneously.

Although an illustrative embodiment of the invention has been shown and described, it is to be understood that various modifications and substitutions may be made by those skilled in the art without departing from the novel spirit and scope of the present invention.

What is claimed is:

1. In an apparatus for the treatment of blood by hemodialysis, having a stack of membrane support plates which support membranes on opposite sides therof and form open volumes between the membrane support plates and the membranes supported thereon, the improvement comprising, in combination:
   a first membrane support plate; a first relatively high flux membrane, with relatively high hydraulic permeability, supported on one side of said first membrane support plate and forming an open volume between said first relatively high flux membrane and said first membrane support plate;
   a first relatively low flux membrane supported on the opposite side of said first membrane support and forming an open volume between said first relatively low flux membrane and said first membrane support plate;
   a second membrane support plate spaced from said first membrane support plate, with a blood path formed in the spacing between said first and second membrane support plates;
   a second relatively high flux membrane, with relatively high hydraulic permeability, supported on one side of said second membrane support plate and forming an open volume between said second relatively high flux membrane and said first membrane support plate;
   a second relatively low flux membrane supported on the opposite side of said second membrane support plate and forming an open volume between said second relatively low flux membrane and said second membrane support plate;
   said open volume between said relatively high flux membranes and the respective membrane support plates comprising a low pressure path to provide significant ultrafiltration;
   said open volume between said relatively low flux membranes and the respective membrane support plates comprising a dialysate solution path to provide significant dialysis and relatively insignificant ultrafiltration; and
   said membrane support plates segregating said open volume between said relatively high flux membranes and the respective membrane support plates from said open volume between said relatively low flux membranes and the membrane support plates.

2. In an apparatus as described in claim 1, said one sides of said membrane support plates being oriented in a common direction whereby said first relatively low flux membrane will face said second relatively high flux membrane on opposite sides of the blood path formed in the spacing between said first and second membrane support plates.

3. In an apparatus as described in claim 1, said low pressure path being adapted for coupling to a vacuum pump.

4. In an apparatus as described in claim 1, said dialysate solution path being adapted for coupling to a supply of dialysate solution.

5. In an apparatus as described in claim 1, said relatively high flux membrane comprising one of the group consisting of polyacrylonitrile and polycarbonate.

6. In an apparatus as described in claim 1, said relatively low flux membrane comprising Cuprophan ®.

7. In an apparatus as described in claim 1, and further including a blood manifolding path extending through said stack; and closing means sealing the membranes on opposite sides of each membrane support plate to each other adjacent said blood manifolding path, said closing means being spaced from each other to define a blood path therebetween and being independent of each other whereby the closing forces generated by one of the closing means on its respective membrane are independent of the closing forces generated by the other closing means on its respective membranes.

8. In an apparatus for the treatment of blood by hemodialysis having a stack of membrane support plates which support membranes on opposite sides thereof and form open volumes between the membrane support plates and the membranes supported thereon, the improvement comprising, in combination:
   a plurality of membrane support plates spaced from each other to form blood paths in the spacing between said membrane support plates;
   a relatively high flux membrane, with relatively high hydraulic permeability, supported on one side of each of said membrane support plates and forming an open volume between said relatively high flux membrane and said membrane support plate;
   a relatively low flux membrane supported on the opposite side of each of said membrane support plates and forming an open volume between said relatively low flux membrane and said membrane support plate;

said one sides of said membrane support plates being oriented in a common direction whereby said relatively low flux membranes will face said relatively high flux membranes on opposite sides of the blood path formed in the spacings between said membrane support plates;

said open volume between said relatively high flux membranes and the respective membrane support plates comprising a low pressure path to provide significant ultrafiltration;

said open volumes between said relatively low flux membranes and the respective membrane support plates comprising a dialysate solution path to provide significant dialysis and relatively insignificant ultrafiltration; and said membrane support plates segregating said open volume between said relatively high flux membranes and the respective membrane support plates from said open volume between said relatively low flux membranes and the membrane support plates.

9. In an apparatus as described in claim 8, a blood manifolding path extending through said stack; closing means sealing the membranes on opposite sides of each membrane support plate to each other adjacent said blood manifolding path, said closing means being spaced from each other to define a blood path therebetween and being independent of each other whereby the closing forces generated by one of the closing means on its respective membranes are independent of the closing forces generated by the other closing means on their respective membranes.

* * * * *